United States Patent [19]

Perry et al.

[11] Patent Number: 5,241,466
[45] Date of Patent: Aug. 31, 1993

[54] SYSTEM FOR ADMINISTERING A CENTRAL DEPOSITORY FOR LIVING WILLS AND OTHER ASSOCIATED INFORMATION

[76] Inventors: Victor A. Perry, 4751 Red's Grade, Carson City, Nev. 89703; Paul F. Oelsner, 2260 Applewood Ct.; Grant P. Anderson, 60483 Meadow Hill Dr., both of Reno, Nev. 89509

[21] Appl. No.: 721,167

[22] Filed: Jun. 26, 1991

[51] Int. Cl.$^5$ .............................. G06F 15/21
[52] U.S. Cl. .................... 364/401; 364/406
[58] Field of Search ............ 364/401, 406, 408

[56] References Cited

U.S. PATENT DOCUMENTS 4,491,725  1/1985  Pritchard .................. 235/375

FOREIGN PATENT DOCUMENTS 2105075  3/1983  United Kingdom .

OTHER PUBLICATIONS

Financial Times (London Edition), Oct. 31, 1985, "Technology: Optical Disk System", p. 1 (abstract only provided).
Business Week (Industrial Edition), Aug. 7, 1989, "This Legal Assistant Can Make or Break a Case", p. 66A (abstract only provided).
Government Computer News, Sep. 16, 1991, "Justices Uses Optical Disks to Store Legal Documents", p. 105 (abstract provided only).
Home Office Computing, vol. 9, No. 4, Apr. 1991, Waters, "Write Your Own Will from the Ground Up", pp. 67-69 (abstract only provided).
Globe & Mail (Toronto, Canada), Oct. 29, 1987, "Computer to Usher in New Era for Organ Donations", p. B19 (abstract only provided).
The Journal of the American Medical Association, vol. 264, No. 4, Jul. 25, 1990, "The National Organ Transplantation Scientific Registry", p. 436 (abstract only provided).
New York Times (National Edition), Oct. 1, 1986, "US Network set up to match organ donors and recipients", p. 131 (abstract only provided).
PTS Prompt Database, DIALOG Accession No. 02200978, Apr. 20, 1989, "U.S. Trust Completes Pilot Test of AGA DISCUS 2001 PC-Based Information And Image Processing Integrated Workstations".
Buyer's Guide to Micro Software Database, DIALOG Accession No. 00012814, 1990, product name: "Legal Records Management Software".
Business Software Database, DIALOG Accession No. 01219169, product name: "Will File 3.1".
Computer Shopper, vol. 11, No. 4, Apr. 1991, Gilliland, "Willmaker 4.0: No Questions, It's the Best", pp. 478-481 (abstract only provided).

Primary Examiner—Roy N. Envall, Jr.
Assistant Examiner—David Huntley
Attorney, Agent, or Firm—Dorr, Carson, Sloan & Peterson

[57] ABSTRACT

A central depository for secure storage and rapid retrieval of important documents and information, such as living wills, durable powers of attorney, testamentary wills, authorization for organ donation, authorization of bone marrow donation, and insurance information. The depository includes a data storage facility having a computer and Write Once, Read Many (WORM) drive CD-ROM player connected to an optical scanner. The documents are scanned by the optical scanner and stored on the CD-ROM player. Other information is entered into data storage facilities connected to the computer. Requests for information can be received by the depository from remote locations by data transmission devices, such as telephone, facsimile, postal service, or electronic mail. The system also provides a procedure for updating the information and documents as legislation regarding the stored information and documents changes. Also, the system monitors for changes in residence which may affect the information and documents.

27 Claims, 6 Drawing Sheets

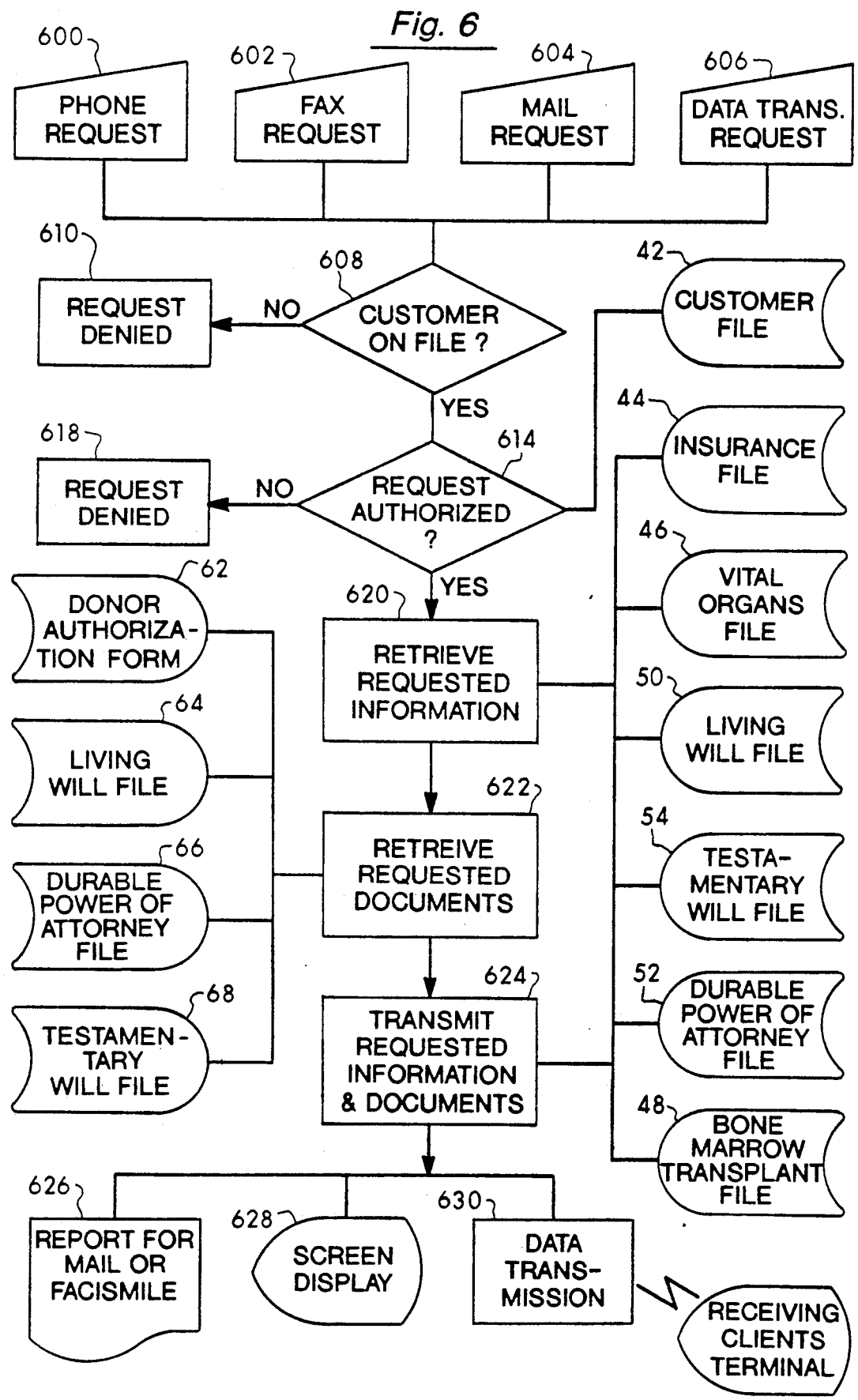

SYSTEM FOR ADMINISTERING A CENTRAL DEPOSITORY FOR LIVING WILLS AND OTHER ASSOCIATED INFORMATION

BACKGROUND OF THE INVENTION

1. Field of the Invention:

The present invention relates to the field of central depositories for living wills, testamentary wills, durable powers of attorney, insurance information and organ donor data banks.

2. Statement of the Problem:

In times of emergencies, there is often an urgent need for immediate access to important documents. For instance, the general public is becoming aware of their right to refuse medical treatment or terminate life support systems, in the event of imminent death or permanent unconsciousness. However, this right needs to be expressed in advance, through documents such as a living will and durable power of attorney.

These documents are typically, if at all, created, executed and filed in a haphazard manner, with little regard to their accuracy or uniformity, or to ease of access, security or to updating the documents for legal sufficiency in case of legislative changes or changes of residential jurisdiction. The documents are created in an individual manner and then filed away where they can be lost or destroyed. At best the documents are stored in a safety deposit box with limited access thereto. Generally, relatively few people provide for ready access to these documents, or other documents, such as living wills, testamentary wills and/or organ and blood marrow donor forms, at the times of crisis when these documents are most needed.

This is particularly true in today's mobile society where catastrophic accidents or illnesses can occur in locations away from home. An individual can be involved in a catastrophic accident or illness in a location far from home, and the treating medical facility will be unable to gain access to the necessary documents. Also, valuable time can be wasted in the instance of organ donations in trying to gain authorization from relatives.

These documents may also need to be periodically reviewed and revised as the laws change or situations are altered. The documents may be legally sufficient at the time of execution, but as legislation changes, the documents may be no longer valid. Also, a document executed in one jurisdiction may not be valid in another jurisdiction where the individual later resides.

In the situation of accidents or death, it may be difficult to verify insurance coverage, including health insurance and life insurance. Life insurance policies are often stored in inaccessible locations, thus slowing the benefit payments. Also, it may be awkward to verify health insurance coverage for treatment in remote locations.

Another related problem is in finding compatible donors for bone marrow transplants. Typically, in the instances where a bone marrow transplant is necessary, the donee must ask for volunteers. There is no central index for potential donors to be cross-typed according to compatibility.

Therefore a need exists for a central depository which can solve these and other problems.

SOLUTION TO THE PROBLEM

The present invention provides a national depository for filing of such documents as living wills, durable powers of attorney and collateral data bases of testamentary wills, insurance information and organ and bone marrow donors.

The present invention provides a data processing system to store such documents as well as information about the individual that may be necessary in times of crises.

The present invention provides a system that can manage these documents and provides information to verify the documents for accuracy and legal requirements.

The present invention provides a system that can periodically review for legislative updates.

The present invention provides a system that can periodically review and verify for changes of address and situations.

The present invention provides a system that can process requests for stored information and retrieve such information for authorized requestors.

The present invention provides a system that can transmit such requested information directly to the requestor.

These and other solutions are provided by the present invention as will become evident from the ensuing description of the invention taken in conjunction with the drawings.

SUMMARY OF THE INVENTION

The present invention provides a central depository for secure storage and rapid retrieval of important documents and information. This includes such items as living wills, durable powers of attorney, testamentary wills, authorization for organ donation, authorization of bone marrow donation, and insurance information.

One preferred embodiment of the present invention includes a data storage facility having a computer and optical storage device connected to an optical scanner. The documents are scanned by the optical scanner and stored in an optical storage facility. Other information is entered into data storage facilities connected to the computer. Requests for information can be received by the depository from remote locations by data transmission devices, such as telephone, facsimile or electronic mail. The depository will process these requests, to verify that the request applies to a customer of the depository, and that the person making the request is authorized to receive the information. The authorized request for information and documents can then be processed and the appropriate information and documents retrieved and transmitted to the person making the request.

The system also provides a procedure for updating the information and documents as legislation regarding the stored information and documents changes. Also, the system monitors for changes in residence which may affect the information and documents.

The system of the present invention provides a secure depository for important information and documents which may be rapidly retrieved from almost any geographical location.

These and other features of the claimed invention will become evident from the ensuing detailed description of a preferred embodiment taken in conjunction with the drawings.

BRIEF DESCRIPTION OF THE DRAWINGS

FIG. 6 is a flow chart of the request processing procedure of the system.

DETAILED DESCRIPTION OF A PREFERRED EMBODIMENT

1. Overview of a Preferred Embodiment

The present invention provides a central depository for important documents, such as living wills (expressing and authorizing the "right to die"), durable powers of attorney and other collateral documents including testamentary wills, authorizations for organ and bone marrow donations, and insurance information. The general public has increasingly become aware of the need to express, in advance, the preference and right to refuse medical treatment in the event of imminent death or permanent unconsciousness. The present invention provides a safe central repository for such "right to die" documents, including living wills and durable powers of attorney and a system for management and retrieval of these documents and associated information. This system is also suited as a repository for related documents such as testamentary wills and authorizations for organ and bone marrow donations as well as information such as health and life insurance.

Figure 1:
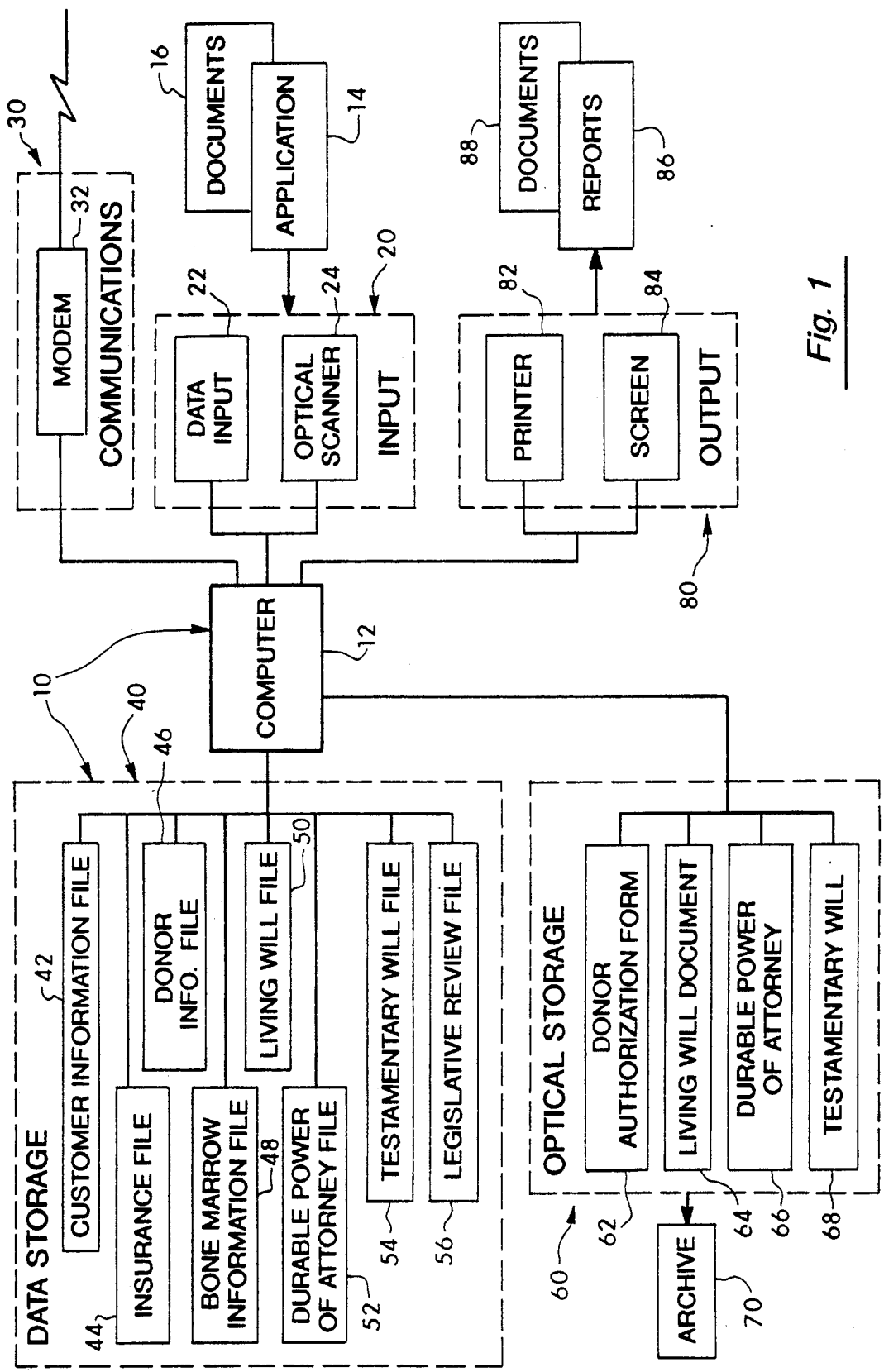
FIG. 1 shows an overview of a preferred embodiment of the present invention.
Figure 2:
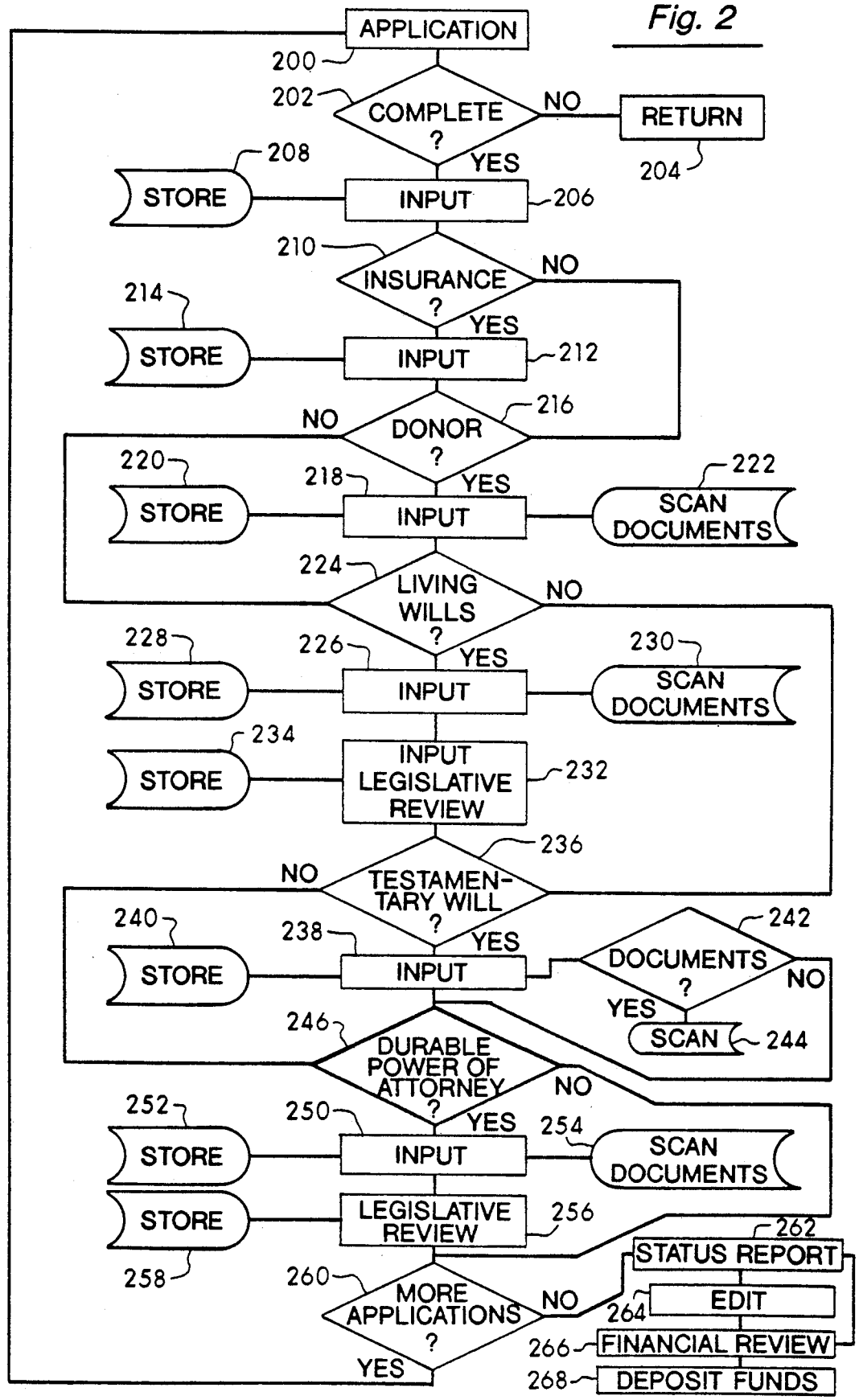
FIG. 2 is a flow chart of the application process of the present invention

A general overview of a preferred embodiment of the present invention is illustrated in FIG. 1. It is to be expressly understood that this descriptive embodiment is for explanatory purposes only and is not meant to limit the scope of the claimed inventive concept. Other variations and embodiments are considered to be within the scope of the inventive concept.

2. System Configuration of a Preferred Embodiment

The central depository 10, shown in FIG. 1, can be physically located at almost any location. The depository includes computer 12 having data input 20 Input 20 includes data input device 22, such as a keyboard or mouse, and optical scanner 24, for processing applications. The application information 14 can be manually entered through the data input device 22 while any documents 16 can be scanned in by optical scanner 24. Communications device 30, which includes modem 3 inputs information into computer 12; in addition, it receives requests for information and documents and transmits information from the system.

The information from the application is verified by computer 12 and stored in data storage 40. Separate files are set up for each customer according to the desired service. Customer document file 42 is set up to store information on each particular customer, such as background information, billing information and identifying information as discussed in greater detail below. Insurance file 44 is set up to store information relating to life insurance and health insurance if the customer desires. Information regarding potential organ donation is stored in donor information file 46. Bone marrow information file 48 is set up for information on potential bone marrow transplant donors. Living will information is stored in living will file 50 and durable power of attorney information is stored in durable power of attorney file 52. Testamentary will file 54 is set up to store information regarding the testamentary will and codicils of the customer. Legislative review file 56 is set up to periodically review and update any necessary information and documents as legislation is updated.

Documents scanned by optical scanner device 24 are stored in optical storage 60. Many jurisdictions are recognizing, for legal purposes, documents stored on a Write-Once, Read-Many Times (WORM) drive CD-player, without requiring production of the original documents. Document stored on WORM-drives are unalterable; therefore, they should be sufficient for legal purposes. Documents relating to authorization for organ donation are stored in donor authorization form file 62. Living will documents are stored in living will document file 64. Durable power of attorney file 66 is set up to store durable power of attorney documents. Testamentary wills are stored in testamentary will file 68.

Archive 70 is available for physically storing the original documents. Archive 70 will typically be a fireproof vault or underground cavern or the like to securely store the original documents.

Depository 10 further includes computer output 80. Output 80 includes printer 82 to print out the stored information, documents 86, and reports 88 and screen device 84. Communications device 30 also can serve as an output device for computer 12 to directly transmit data to remote locations.

Computer 12 includes operating systems, discussed in greater detail below, to verify the applications for accuracy and completeness, for entering information and documents to the appropriate files, and for processing requests for information and documents. Computer 12 also periodically reviews the files and documents for legislative updates and for jurisdictional requirements in regard to customer changes of residences. Billing systems are also in place to alert customers to upcoming fees and to bill the customers for such fees. The system is also capable of updating customer information as necessary and purging the depository of any information and documents regarding inactive customers.

Processing the application:

Depository 10 typically operates as illustrated in FIGS. 2-5. As indicated in the chart illustrated in FIG. 2, the customer sends to depository 10, as indicated in block 200, a completed application form including information, such as the customer's name, date of birth, social security number, current address, mother's maiden name, next of kin, and insurance information, as well as the necessary documents, such as a living will, durable power of attorney, testamentary will and authorization for donation of organs and bone marrow. This application is received at the receiving office of depository 10 where it is processed, at decision block 202, either manually or by a computerized system. The information is checked for completeness as well as obvious errors. If the information is incomplete or in error, the application, at block 204, is returned to the customer with a request for additional information. Once the application is complete, the information and documents are entered, at block 206, into the depository.

A customer information file 42 is created for each customer and a unique file number is assigned with a code identifying the state of residence of the customer. This could be the customer's social security number or a number generated by the depository. Initially, the customer's reference information is entered into the system. This reference information includes such information as the customer's name, date of birth, social security number, current address and mother's maiden name or other significant identifying information. This information, at block 208, is stored in customer information file 42.

The system then moves to decision block 210 for insurance information. If the customer does not desire insurance information to be stored, then the system will move on to decision block 216 for organ donor authorization. However, if requested by the customer, insurance information is entered, at block 212, into the system. The insurance information will be stored, at block 214, in insurance file 44. This will allow for the retrieval of critical information for prompt notification of the insurance company at the time of need or death and to insure that all benefits or proceeds are made immediately available to the appropriate parties.

The next step, at decision block 216, is to determine whether organ and bone marrow donation is to be authorized. If the customer does not wish to authorize organ donation, then the system moves to decision block 224 for living wills. However, if the customer wishes to authorize organ donation, then the system, at block 216, will identify which vital organs are desired to be donated as well as the possible use of the customer's body for potential scientific study. This information is stored, at block 220, into donor information file 46. Donor authorization forms, if necessary, are scanned at block 222 and stored in optical storage 60 in donor authorization form file 62.

Also, at block 218, if the customer wishes to be indexed for potential bone marrow transplants, then this information will be stored, again at block 220, in bone marrow information file 48. This information will be available to authorized individuals who are on a list of those individuals who have been typed for bone marrow transplants and are willing to be available for such transplants This information would be available immediately to streamline the matching of potential donors and recipients.

The system, at decision block 224, determines if living will information and documents are to be entered into the system. If the customer does not desire this service, then the system moves to decision block 236 for testamentary wills If the customer wishes to store living will documents, then the system inputs living will information at block 226 into the system. The living will expresses the customer's right and preference to have medical support terminated under certain detailed conditions, involving imminent death or permanent unconsciousness. Information regarding the customer's living will is stored at block 228 into living will file 50. The living will documents are stored, at block 230, into optical storage 60, in living will document file 64.

The system next inputs, at block 232, legislative review information into the system. The legal requirements for living wills may differ from state to state. Therefore the living will information is checked relative to the requirements of the state in which the customer resides This information is readily flagged by the unique identification code on the customer's file. Also, the system is able to verify, as discussed in greater detail below, the customer's documents for validity as legislation is updated. This information is stored, at block 234, in legislative review file 56.

The system, at decision block 236, determines if the customer wishes information and documents relating to their testamentary will and codicils stored. The system moves to decision block 246 if the customer this service, then information regarding the testamentary will and codicils is entered, and then stored at block 240 into testamentary will file 54. At decision block 242 the system determines whether there are documents to be scanned. If not, then the system moves on to decision block 246 for durable power of attorney. If there are documents to be scanned, then these documents are stored, at block 244, into optical storage 60 in testamentary will file 68.

The system at block 246 determines whether to input information and documents relating to the durable power of attorney. This typically is a companion document to the living will and testamentary will A durable power of attorney creates a power of attorney which will survive incapacitation of the customer. This is necessary in order for the appointee to be able to execute the wishes of the living will. If storage of a durable power of attorney is not desired, then the system moves on to decision block 260. If a durable power of attorney is to be stored, then information and documents regarding the durable power of attorney is entered, at block 250. The information is stored, at block 252, into durable power of attorney file 52. The documents are scanned, at block 254, into optical storage 60, in durable power of attorney file 66.

The system inputs, at block 256, legislative review information regarding the durable power of attorney. Legal requirements differ from jurisdiction to jurisdiction and may periodically be revised. The system verifies the accuracy of the customer's durable power of attorney according to their residential jurisdiction and periodically verifies these documents as legislation is revised. This information is stored, at block 258, into legislative review file 56.

The original documents are either sent back to the customer (not shown), or if the customer requests, stored in an safe and secure archive 70 operated by the depositary.

The system, at decision block 260, determines if there are any more applications to be processed. If there are more applications to be processed, then the system moves back to block 200 and repeats the process as necessary. If there are no more applications waiting to be processed, then the system prepares a status report, at block 262. The system verifies that this report is correct and moves to block 266. If necessary, the report is edited, at block 264, then the system moves to block 266.

The system at block 266 reviews the financial status of the processed applications. The funds that were generated by the processing of the applications are then deposited, at block 268, in an appropriate location.

It is to be expressly understood that the embodiment described above is for explanatory purposes and is not meant to limit the scope of the inventive concept. For instance, the system of the present invention can process the information in any number of sequential steps and in any order of processing the information and documents.

Updating the system:

The system of the present invention provides the capability to periodically and automatically update the status of the files stored therein. The system does this by three procedures.

Figure 3:
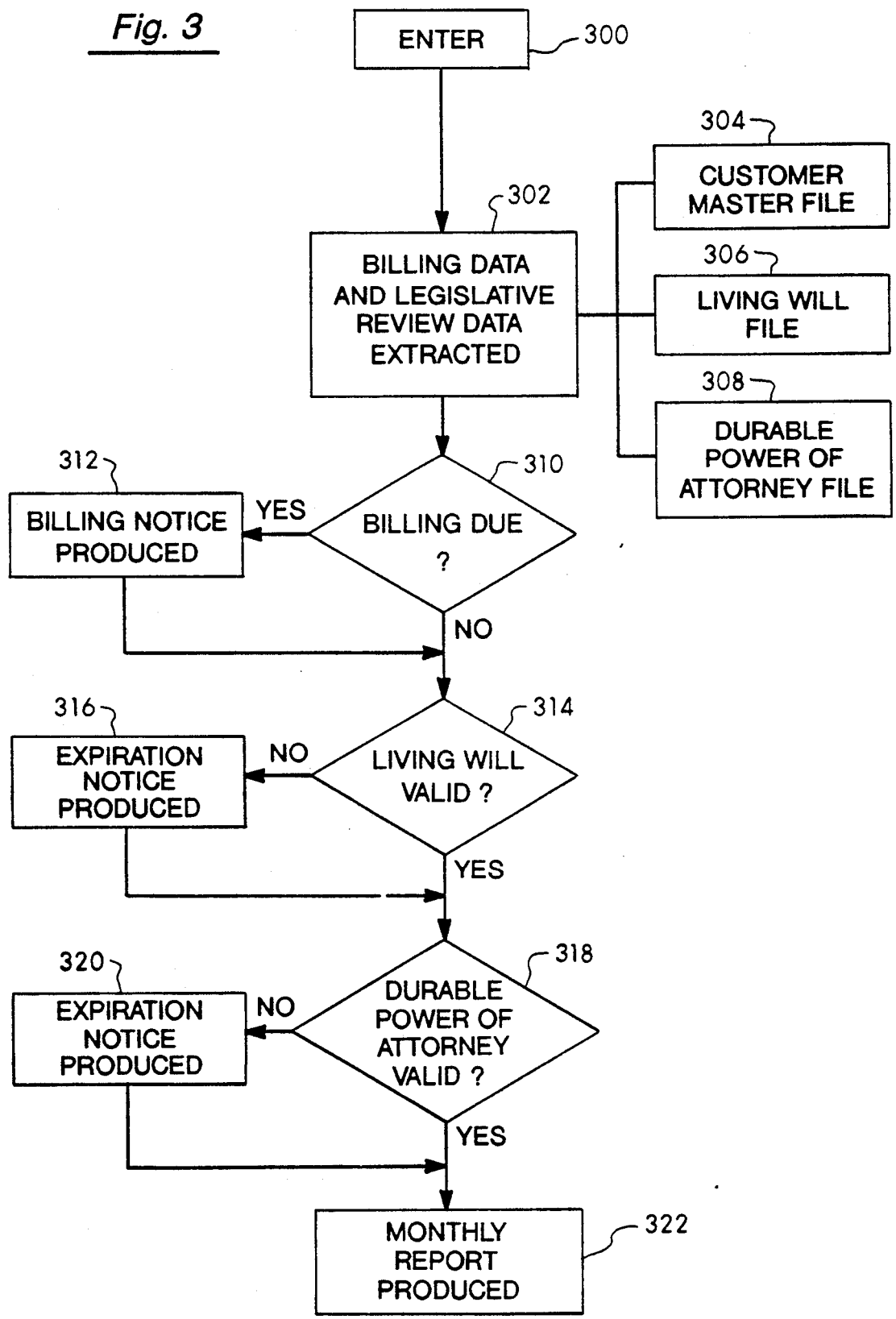
FIG. 3 is a flow chart of the periodic updating of the system.

The first procedure, shown in FIG. 3, updates the legislative review data periodically. As the statutory requirements evolve in each jurisdiction, the system will note these changes. Periodically, or as legislation affecting the validity of stored documents is revised, the system will enter the customer files, as shown in block 300, in FIG. 3. The system, in block 302, will enter each customer's files, and, at blocks 304, 306, and 308, the system will extract billing data and legislative review data therefrom.

The system then enters decision block 310 to determine if billing is due to the customer. If not, then the system proceeds to decision block 314. If the customer is due to be billed, then a billing notice is produced at block 312. The system then moves on to decision block 314.

The system at decision block 314 determines if the living will is still valid after the legislative revisions. If the living will is still valid, then the system moves onto decision block 318. If the living will is no longer valid, then the system at block 316 produces an expiration notice for the customer. The system then moves onto decision block 318.

The system at decision block 318 determines if the durable power of attorney is still valid after the legislation revisions. If the durable power of attorney is still valid, then the system moves onto block 322 to produce a monthly report. If the durable power of attorney is no longer valid, then the system at block 320 produces an expiration notice. The system then moves onto block 322.

At block 322, the system produces a monthly report of all activities generated by the system and the status of the files and documents.

Figure 4:
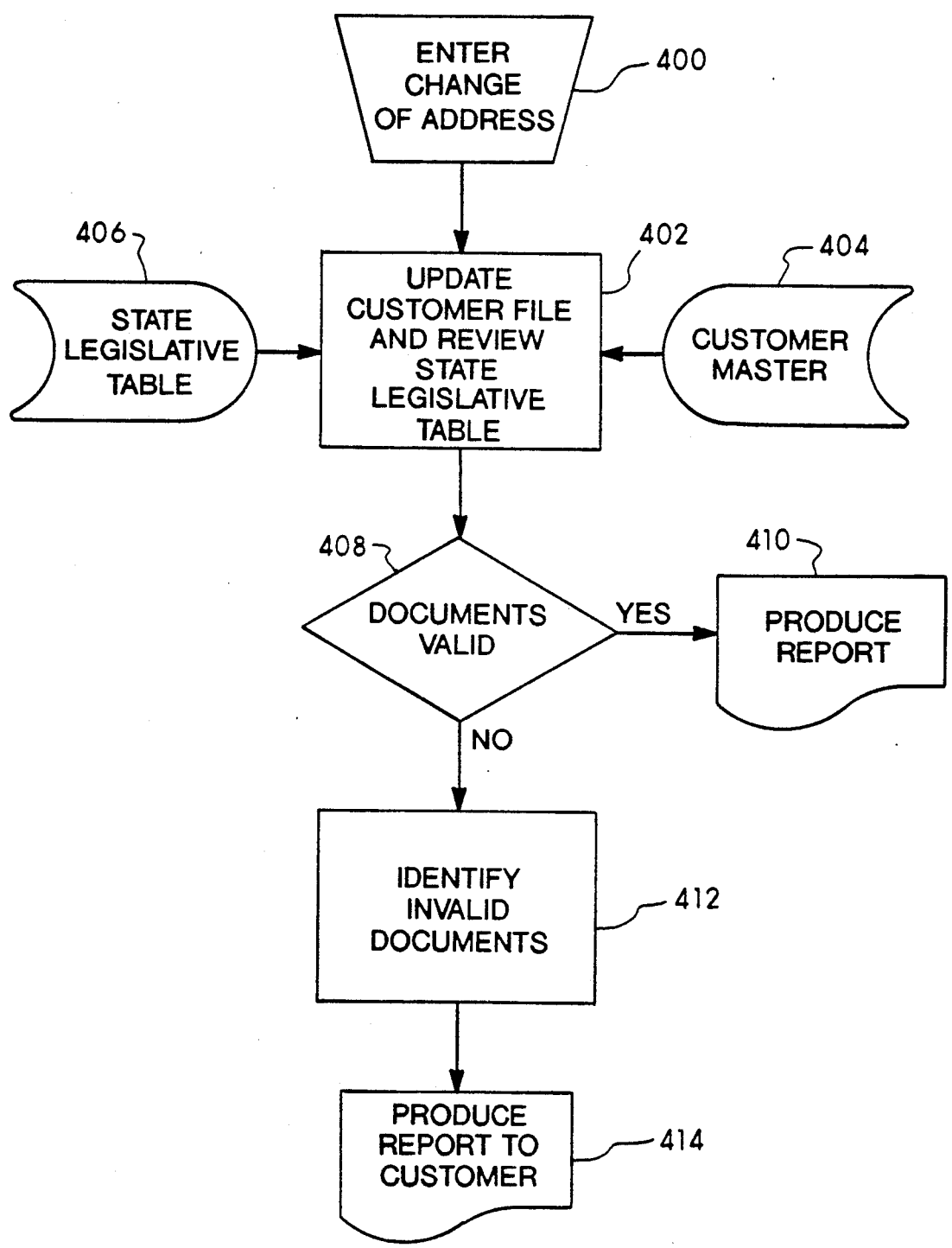
FIG. 4 is a flow chart of the updating of documents after a change of address.

The second updating procedure also occurs, shown in FIG. 4, automatically. Once a customer changes address and sends in a change of address to the system, this change of address is entered into the system, as indicted in block 400. Customer information file 42, in block 404, is retrieved, and the new change of address, in block 402, is updated. Also in block 402, information from legislative review file 56, retrieved in block 406, is reviewed. The system, in block 408, reviews the documents which have been previously stored to determine whether they are still valid in the new residential jurisdiction. If the documents are still valid, then the system, in block 410, produces a report to this effect. If the documents are no longer valid, then the system in block 412 identifies the documents which are no longer valid. A report, in block 414, is produced and sent to the customer identifying the invalid documents and requesting new documents to be executed.

Figure 5:
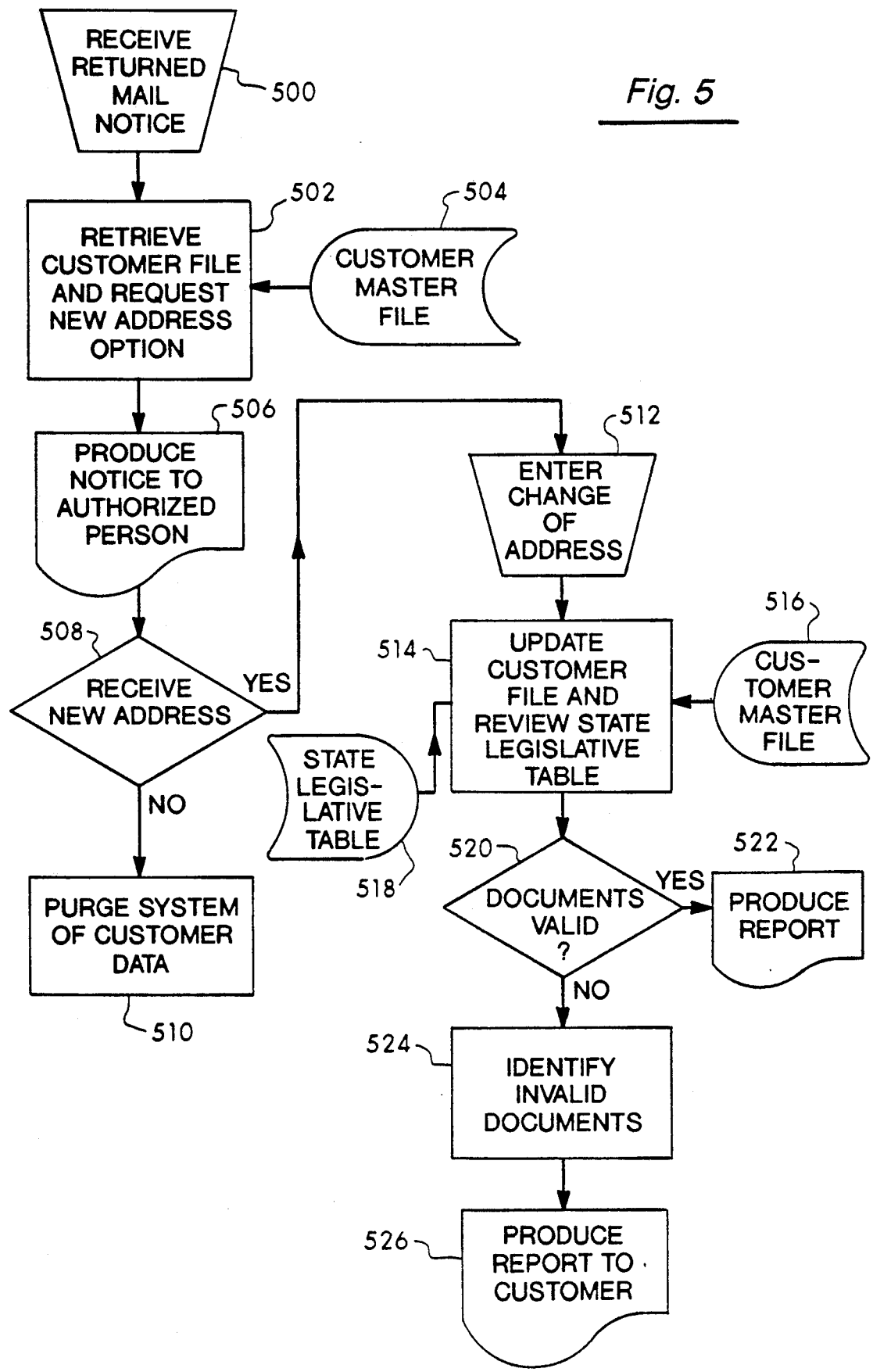
FIG. 5 is a flow chart of the tracing procedure of the system.

The third procedure, illustrated in FIG. 5, involves a tracing procedure for customers who have moved without notifying the depository of their change in address. Each customer is periodically billed for the costs of the depositary service A returned mail notice is entered into the system, at block 500, if the bill is returned because the customer is no longer at that address. The system then, at block 502, retrieves customer information file 42, in block 504, and requests the new address option. The new address option includes the name and address of a person or entity that the customer designated who will provide notification of the whereabouts of the customer. Typically this will be a close relative, or someone to be notified in the event of an emergency. The system produces a notice, in block 506, to the designated person or entity requesting a new address for the customer. After a predetermined passage of time, the system moves to decision block 508 to determine whether a new address for the customer has been received. If a new address has not been received, then the system moves to block 510 to purge the system of the customer data and documents. Normally the system will move the information files and document files to an inactive status for a designated period of time after which the system will purge all information and documents from the system.

If a new address for the customer is received, then the system, in block 512, will enter the change of address into the system. The customer information file 42, in block 516, will be retrieved and updated, in block 514, with the new address. In block 514, the system will also retrieve legislative review file 56 to review the jurisdictional requirements for the stored documents. In decision block 520, the system will determine whether the documents are still valid in the new residential jurisdiction. If the documents are still valid, then in block 522 the system will produce a report to that effect.

If the documents are no longer valid, then, in block 524, the system will identify which documents are no longer valid. The system will then, in block 526, produce a report to the customer identifying the invalid documents and requesting new executed documents to be sent to the depository.

Utilization of these procedures provides the customer with automatic and periodic verification and update on the status of the information and documents stored in the depository.

Processing requests for information:

The depository system provides rapid processing of requests for the information and documents stored there. The processing operation is shown in FIG. 6. A telephone request, in block 600, facsimile request, in block 602, mail request 604, or other data transmission request 606, for information or documents regarding a particular customer is received and entered into the system.

The system, in decision block 608, first verifies that the person on which the information or documents is requested is a customer of the depository. If the person is not a customer, then, in block 610, the request is denied. If the person is a customer, then, in block 614, the system verifies that the person or entity making the request is authorized to receive the information and documents. This is done by retrieving customer information file 42 and checking for prior authorization or for prior authorized procedures. If the person or entity making the request is not authorized to receive the information or documents, the request, in block 618, is denied.

Once a request has been authorized, then the system moves to block 620 to retrieve the requested information from insurance file 44, organ donation file 46 bone marrow transplant file 48, living will file 50, durable power of attorney file 52 or testamentary will file 54. The system then in block 622 retrieves requested documents from authorization form file 62, living will document file 65 durable power of attorney file 66 or testamentary will file 68.

The retrieved information or documents are then, in block 624, transmitted via the appropriate transmitting device to the person or entity making the request. Documents and reports can be transmitted in block 626 via mail or facsimile transmission. Information can also be transmitted via screen display, in block 628, directly over telephone requests. Also the information data can be directly transmitted over the communications device 30, in block 630, to a receiving terminal.

Billing systems are utilized (not shown) to charge the appropriate fees for the services.

Examples of the processing of requests for various information and documents are described below. It is to be expressly understood that these examples are for descriptive purposes only and are not meant to limit the scope of the claimed inventive concept. The system of the present invention is capable of various embodiments and modifications and the below described examples are for explanatory purposes only.

Example of request for living will:

A request for the living will documents is received by the processing system by a toll-free 800 number, facsimile, mail, electronic mail or other data transmission devices. The request is checked against the customer file. If the information is on file, then the requesting entity can be notified, if a toll-free 800 number was used, to call a "900" telephone number, for billing purposes, or other payment/billing device to receive the information.

After the requesting entity has done so, then the processing system verifies that the requesting entity is authorized to receive the information and documents. This may be by prior authorization contained in the customer's files, or by operation of law.

If the requesting entity is authorized to receive the information and documents, then the information is retrieved and transmitted to the requesting entity. This can be by electronic transmission, by telephone, by facsimile or other data transmission devices. The documents can be retrieved from the optical storage device and mailed to the requesting entity.

The center will purge the information and documents from the system, once it has been notified that the customer is deceased.

Example of inquiry for organ donation: customer's desire to donate organs or body portions should the customer be declared dead. At the appropriate time, a medical facility may call an "800" number to verify if a patient is a customer of the center. This can be done by an automatic answering device. If the center verifies that the patient is a customer, then the medical facility is given further instructions to call a "900" number or another data transmission device.

The medical facility will provide pertinent information as to the customer, such as name, social security number, date of birth and the like. If that customer has indicated their desire to be a donor, then the center will provide to the requesting facility, if authorized, a copy of the donor card and information by electronic transmission or other data transmission devices. If necessary, a certified copy of the original document will be provided from the archives or from the optical data storage.

Example of request of compatibility typing:

The appropriate entity, normally a medical facility or medical doctor, calls the "800" number for inquiries as to whether a person is a customer of the center, in the case of organ donation, or if a specific Human Leukocyte Antigen (HLA) type is available, for bone marrow donation. The caller can ascertain from the answering device whether a particular person is a client of the center, or if there is a particular HLA type noted for potential bone marrow donation.

In the event that there is an affirmative answer to the caller's inquiry, the caller will be instructed to call a "900" number to make the desired request for information or documents. The caller will provide information, including the identity of the caller and reason for requesting the information. The system will verify to ascertain whether the caller is authorized to receive the requested information or documents, either by prior authorization from the customer's files or by operation of law.

If the caller is authorized to receive the information, then the system will verify that the customer has requested that information regarding their Human Leukocyte Antigens (HLA) typing be provided to appropriate medical facilities or doctors. The HLA typing provides an indication of the compatibility between potential organ donors and recipients and potential bone marrow donors and recipients.

The customer can also indicate that they be notified for permission prior to such information being provided. If the request is authorized, then upon payment, via "900" telephone charge or other payment system, the information is transmitted to the caller.

Example of request for testamentary will:

The caller calls the "800" number to ascertain whether a person is a customer of the center. The individual can ascertain from the answering device whether a particular person is a customer of the center.

In the event that there is an affirmative answer to the individual's inquiry, the individual will be instructed to call a "900" number to make the desired request for information or documents. The caller will provide information, including the identity of the caller and reason for requesting the information. The system will verify to ascertain whether the caller is authorized to receive the requested information or documents, either by prior authorization from the customer's files or by operation of law.

If the caller is authorized to receive the information, then a copy of the information, such as the testamentary will, is transmitted to the caller after a charge has been made via the "900" telephone service.

The original of the testamentary device, or a certified copy, can be provided upon receipt of a certified copy of the death certificate of the customer. The death certificate information will be entered into the system and the customer will be removed from the active files to the inactive files, and eventually purged from the system.

If the caller is not authorized to receive the information, then they can send a written request stating reasons for needing the information, a certified copy of the death certificate, and the appropriate fee. A copy of the testamentary device may then be transmitted to the requestor.

Example of request for insurance information:

The caller calls the "800" number to ascertain whether a person is a customer of the center. The individual can ascertain from the answering device whether a particular person has information, such as a Living Will, Durable Power of Attorney, insurance information, organ donation information or testamentary will, stored at the center.

In the event that there is an affirmative answer to the individual's inquiry, the individual will be instructed to call a "900" number to make the desired request for information or documents. The caller will provide information, including the identity of the caller and reason for requesting the information. The system will verify to ascertain whether the caller is authorized to receive the requested information or documents, either by prior authorization from the customer's files or by operation of law.

If the caller is authorized to receive the information, then a copy of the information, such as health insurance if the customer has been in an accident or sudden illness, is transmitted to the caller after a charge has been made via the "900" telephone service.

Likewise, life insurance policy coverage can be ascertained via the same procedure. Also, once a certified copy of the death certificate is provided to the center, a copy of the life insurance policy, or the original if necessary, can be transmitted to the beneficiaries.

The present invention provides a central depository for providing secure storage and rapid access to important documents and information, and a system for administering this depository. The system as claimed is not meant to be limited to the above description of a preferred explanatory embodiment, but encompasses other embodiments and modifications. The claimed invention is not meant to be limited for use with only the above described documents and information but further encompasses other documents and information as the need arises.

We claim:

1. A system for administering a central depository for living wills and other associated documents and customer information for health care purposes, said system comprising:
   data storage means for storing documents and customer information, said documents including said living wills and other associated documents;
   means for entering said documents into said data storage means;
   means for entering said customer information into said data storage means;
   means for verifying that said documents fulfill the legal requirements of said customer's residential jurisdiction;
   means for periodically updating said legal requirements and verifying that said documents still fulfill the legal requirements of said customer's residential jurisdiction;
   means for processing requests for said documents and said customer information from said data storage means;
   means for retrieving said documents and customer information in response to said requests; and
   means for transmitting said requested documents and customer information.

2. The system of claim 1 wherein said documents include durable powers of attorney for health care purposes.

3. The system of claim 1 wherein said other associated documents further include testamentary wills, insurance policies and authorization forms for organ and bone marrow donation.

4. The system of claim 3 wherein said system further comprises means for entering information regarding potential organ and bone marrow donors of said customers; and
means for indexing said information regarding organ and bone marrow donors of said customers according to specific types.

5. The system of claim 1 wherein said means for entering said documents include an optical scanning device.

6. The system of claim 5 wherein said data storage means include a CD-ROM player device for storing said documents scanned by said optical scanning device.

7. The system of claim 1 wherein said system further includes means for verifying said documents and said customer information for completeness, for errors, and for legislative changes.

8. The system of claim 1 wherein said system further includes means for updating changes of said residential addresses of said customers.

9. The system of claim 1 wherein said system further includes
   means for preparing billing information in regard to said customers information as well as the current status of said stored documents and customer information; and
   means for providing said billing information and status to said customer.

10. The system of claim 1 wherein said system further includes means for updating any new customer information and means for purging information relating to inactive customers from said system.

11. The system of claim 1 wherein said means for processing requests includes:
   means for receiving said request for information and documents pertaining to a particular customer;
   means for verifying that information is present in said data storage means for said particular customer;
   means for retrieving said requested information and documents from said data storage means; and
   said transmitting means delivering said requested information and documents to the entity making said request.

12. The system of claim 11 wherein said means for processing requests further includes:
   means for verifying that said entity making said request is authorized to receive said requested information prior to transmitting said requested information and documents.

13. The system of claim 1 wherein said means for transmitting said information includes:
   means for transmitting data to a remote data receiving terminal.

14. A system for administering a central depository for living wills, durable powers of attorney for health care purposes, and other associated documents and customer information; said system comprising:
   data storage means for storing documents and customer information, said documents including said living wills, durable powers of attorney, and other associated documents;
   optical scanning means for entering said documents into said data storage means for storage;
   means for entering said customer information into said data storage means for storage;
   means for receiving requests for information and documents pertaining to a particular customer;
   means for verifying that information is present in said data storage means for said particular customer;
   means for verifying that the requestor is authorized to receive the requested information and documents;

means for verifying said information and documents for completeness, errors, and that said documents fulfill any jurisdictional legal requirements;

means for periodically updating said verification for legal requirements;

means for retrieving the requested information and documents; and means for transmitting the requested information and documents to said requestor.

15. The system of claim 14 wherein said system further comprises:

means for updating information relating to customers having documents and information stored in said system; and means for updating legal requirements for each customer.

16. The system of claim 14 wherein said system includes:

means for preparing billing information for said customers;

means for preparing status reports for said customers;

means for updating information relating to said customers; and means for purging the system of documents and information of inactive customers.

17. A method of administering a central depository for living wills, durable powers of attorneys, and other associated information, said method comprises the steps of:

processing an application from a customer;

entering documents pertaining to said customer into an archival system, said documents including said living wills and said durable powers of attorney, wherein said step of entering documents into an archival system including the steps of:

(a) scanning said documents by an optical scanning device; and (b) storing said scanned documents in a data storage means;

entering information regarding said customer into said data storage means; wherein said step of entering information regarding said customer into said data storage means further includes the steps of:

(a) periodically entering information regarding legislative review pertaining to said documents into said system; and (b) periodically verifying the legal sufficiency of said documents in response to said legislative review information;

processing requests for documents and information regarding said customer;

retrieving documents and information in response to said requests;

transmitting said requested documents and information to the entity making said requests.

18. The method of claim 17 wherein said step of processing an application from a customer includes the steps of:

verifying that said application is complete;

verifying that said application is error-free; and verifying that any documents to be stored are legally sufficient.

19. The method of claim 17 wherein said step of storing said scanned documents in said data storage means includes storing said scanned documents in a CD-ROM player.

20. The method of claim 17 wherein said step of processing requests for information and documents of a particular customer includes the steps of:

verifying that documents and information regarding that particular customer exists in the archival system or the data storage means; and verifying that the request is authorized.

21. The method of claim 17 wherein said step of processing requests for documents and information includes the steps of:

receiving said request for documents and information;

verifying that documents and information for a particular customer is stored in said archival system or said data storage means;

confirming to the entity requesting the documents and information that such documents and information exist; and notifying said entity of the procedure and charge to receive said documents and said information.

22. The method of claim 21 wherein said step of processing requests for documents and information includes the step of:

verifying that the entity making the request is authorized to receive said requested information and documents.

23. The method of claim 17 wherein said step of transmitting said information and documents includes:

transmitting said information and documents directly to a remote location.

24. A method of administering a central depository for living wills, durable powers of attorney, and other associated information, said method comprises the steps of:

processing an application from a customer;

entering documents pertaining to said customer into an archival system, said documents including said living wills and said durable powers of attorney;

entering information regarding said customer into a data storage system;

processing requests for documents and information regarding said customer;

retrieving documents and information in response to said requests;

transmitting said requested documents and information to the entity making said requests;

periodically verifying the place of residence of said customers;

updating any changes of address of said customers; and reviewing said documents and information for legal sufficiency in the new residential jurisdiction.

25. The method of claim 24 wherein said step of periodically verifying the place of residence of said customers further includes:

tracing any change of address by contacting an authorized person in said customer's information for a new change of address.

26. The method of claim 25 wherein said method further comprises:

placing any customer's information and documents in an inactive file should the customer's location be unable to be verified; and after a predetermined amount of time, purge said customer's information and documents from said inactive files.

27. The method of claim 24 wherein said method further comprises:

indexing bone marrow type and organ types of any customer who desires to be a potential donor; and providing the indexed information to appropriate entities for possible cross-matching.

* * * * *